United States Patent [19]

Lagerwaard et al.

[11] Patent Number: 5,069,809

[45] Date of Patent: * Dec. 3, 1991

[54] ENZYMATIC DETERGENT AND BLEACHING COMPOSITION CONTAINING A SPECIFIC RDNA TECHNIQUE CLONED LIPASE

[75] Inventors: Cornelis A. Lagerwaard, Hellevoetsluis; Johannes M. Cornelissen, Vlaardingen; Ton Swarthoff, Hellevoetsluis; Jan Klugkist, Vlaardingen, all of Netherlands; David Thom, Parkgate, England

[73] Assignee: Lever Brothers Company, Division of Conopco, Inc., New York, N.Y.

[ * ] Notice: The portion of the term of this patent subsequent to Sep. 6, 2005 has been disclaimed.

[21] Appl. No.: 541,184

[22] Filed: Jun. 19, 1990

Related U.S. Application Data

[63] Continuation of Ser. No. 349,030, May 9, 1989, abandoned.

[30] Foreign Application Priority Data

May 9, 1988 [GB] United Kingdom ................. 8810954

[51] Int. Cl.$^5$ ....................... C11D 3/386; C11D 3/39; C11D 3/395
[52] U.S. Cl. ................................ 252/174.12; 252/95; 252/100; 252/142; 252/186.1; 252/551; 252/558; 252/DIG. 12
[58] Field of Search .................. 252/DIG. 12, 174.12, 252/95, 99, 100, 186.1, 136, 532, 551, 558, 142

[56] References Cited

U.S. PATENT DOCUMENTS

| | | | |
|---|---|---|---|
| 4,769,173 | 9/1988 | Cornelissen et al. | 252/174.12 |
| 4,861,509 | 8/1989 | Cornelissen et al. | 252/174.12 |

FOREIGN PATENT DOCUMENTS

| | | |
|---|---|---|
| 1012476 | 6/1977 | Canada . |
| 0271152 | 6/1988 | European Pat. Off. . |
| 0305216 | 3/1989 | European Pat. Off. . |

OTHER PUBLICATIONS

European Search Report for EP 89 304620, 8/1/89.
"Biotechnology Newswatch", 3/7/'88, p. 6.
Research Disclosure (RD) #0290056, 6/88, (abstract).

*Primary Examiner*—Paul Lieberman
*Assistant Examiner*—A. Beadles-Hay
*Attorney, Agent, or Firm*—Ronald A. Koatz

[57] ABSTRACT

An enzymatic detergent and bleaching composition contains a bleaching system which is stronger than the sodium perborate/TAED system. In such a composition a lipase is employed which is produced by cloning, by rDNA technique, the gene which encodes the lipase produced by the fungas *Humicola lanuginosa* and expressing that gene in *Aspergillus oryzae* as host. The lipase is used in an amount giving a lipolytic enzyme activity of from 100 to 0.005 lipolytic units/mg of the composition.

6 Claims, No Drawings

ENZYMATIC DETERGENT AND BLEACHING COMPOSITION CONTAINING A SPECIFIC RDNA TECHNIQUE CLONED LIPASE

This is a continuation application of Ser. No. 349,030, filed May 9, 1989.

The present invention relates to an enzymatic detergent and bleaching composition comprising as essential ingredients a lipolytic enzyme and a bleaching system.

Detergent compositions comprising lipase are known. For example GB 1 372 034 (Unilever) discloses lipase from Pseudomonas in specific nonionic-containing detergent compositions for soaking fabrics.

U.S. Pat. No. 3,950,277 (Procter & Gamble) also describes fabric-soaking compositions: the described compositions comprise lipase and lipase activators and a number of lipases from microorganism and other sources are mentioned: those particularly mentioned as preferred are Amano CE, Amano M-AP, Takeda 1969-4-9, and Meito MY-30 lipases, but no indications are given of the form in which the lipase is to be prepared or used.

U.S. Pat. No. 4,011,169/NL 74 08763 (Procter & Gamble) describes the use of a similar range of enzymes in the preparation of additives for washing agents (detergent compositions).

Examples of known lipase-containing detergent compositions are provided by EP 0 205 208 and 0 206 390 (Unilever), which relate to lipases related to those from Ps. fluorescens, P gladioli and Chromobacter in detergent compositions.

EP 0 214 761 (Novo) and EP 0 258 068 (Novo), each give detailed description of lipases from certain microorganisms, and also give certain uses in detergent additives and detergent compositions for the enzymes described. EP 0 214 761 gives detailed description of lipases derived from organisms of the species Pseudomonas cepacia, and certain uses therefor. EP 0 258 068 gives detailed description of lipases derived from organisms of the genus Thermomyces/Humicola, and certain uses therefor.

Also believed to be in use in certain areas is a lipase-containing granular detergent composition containing about 37% detergent actives including 5% nonionic detergent and the remainder substantially anionic detergent, about 16% zeolite, about 60 LU/g lipase, plus protease and other normal detergent additives.

Further examples of known lipase-containing detergent compositions are provided by JA 63-078000 (1988) (Lion Corp/K Mukoyama et al) which discloses properties and uses of a Pseudomonas lipase, including use in a lipase-containing system based on 10–40 % surfactant (e.g., sodium C14-C18 alpha-olefin sulphonate), as well as other conventional detergent ingredients.

In EP 0 268 456 (Clorox), there is described in connexion with Table 10(b) an experimental washing solution containing lipase and about 1 microgram/ml sodium dodecyl sulphate.

In U.S. Pat. No. 4,707,291 (hereby incorporated by reference herein), detergent compositions have been described which contain a special class of lipolytic enzymes. These compositions may also contain a bleaching agent such as sodium perborate, either as such or in admixture with a low temperature bleach activator e.g., tetraacetyl-ethylene-diamine (TAED). The lipases mentioned in U.S. Pat. No. 4,707,291 are significantly less affected by a bleaching system than other lipases. These bleaching systems comprise sodium perborate and TAED.

We have now surprisingly found that a certain type of lipase, defined herein below, is quite compatible with bleaching systems which are stronger than the sodium perborate/TAED system, such systems being defined in more detail hereafter. This type of lipase is more stable in the presence of these bleaching systems than some of the lipases mentioned U.S. Pat. No. 4,707,291 and is in particular more stable than the lipases mentioned in U.S. Pat. No. 4,707,291 in the presence of proteases in these bleaching systems.

The lipase used in the present invention is a lipase produced by cloning, by rDNA technique, the gene encoding the lipase produced by the fungus *Humicola lanuginosa* and expressing the gene in *Aspergillus oryzae* as host. This product is manufactured and commercially available from Novo Industri A/S, Denmark, under the trade name Lipolase (see 'Biotechnology Newswatch', published 7th March 1988, page 6). In the relevant manufacturer's technical leaflet on Lipolase (Trade Mark) it is said that this lipase is not stable in the presence of e.g., hypochlorite as bleaching agent.

Equivalence of a lipase enzyme produced by rDNA technique to the lipase defined above can be determined in practice for example by an immunological reaction of identity between the two lipase materials and/or by determination of substantial aminoacid sequence homology therebetween. In some such equivalent lipases, of which the use is within the scope of the invention, the pattern of glycosylation of the lipase protein differs.

EP 0 305 216 (Novo) also describes suitable lipase enzymes for use in the practice of this invention, and is hereby incorporated by reference herein.

The lipase used in the present invention is included in the detergent and bleaching composition in such an amount that the final composition has a lipolytic enzyme activity of from 100 to 0.005 LU/mg, preferably 25 to 0.05 LU/mg of the composition.

A Lipase Unit (LU) is that amount of lipase which produces 1/micromol of titratable fatty acid per minute in a pH stat. under the following conditions: temperature 30° C.; pH=9.0; substrate is an emulsion of 3.3 wt. % of olive oil and 3.3% gum arabic, in the presence of 13 mmol/l Ca++; and 20 mmol/l NaCl in 5 mmol/l Tris-Buffer. An alternative definition of the lipase unit is given in EP 0 258 068 (Novo), which mentions (inter alia) lipases suitable for use in the practice of this invention and is hereby incorporated by reference.

Naturally, mixtures of the above lipase with other known lipases can be used. The lipase(s) can be used in its (their) non-purified form or in a purified form, e.g., purified with the aid of well-known adsorption methods, such as phenyl sepharose adsorption techniques.

The bleaching system used according to the present invention is stronger than the sodium perborate/TAED system. This latter system, through a perhydrolysis reaction, forms a peroxyacid, i.e., peracetic acid, but at a rather low rate. The bleaching systems according to the present invention must be stronger than this sodium perborate/TAED system, by which is to be understood that the system either is based on a peracid (inorganic or organic) which is stronger than the peracetic acid or yields, on perhydrolysis, an organic peracid, including peracetic acid, faster than the sodium perborate/TAED system. The bleaching system may consist of a bleaching agent as such or may consist of a bleaching agent together with a bleach precursor. As bleaching agent as such alkali metal monopersulphates, furthermore organic peracids such as diperoxy dodecanedioic acid, deperoxy tetradecanedioic acid, diperoxyhexadecane dioic acid, mono- and diperazelaic acid, mono- and diperbrassylic acid, monoperoxy phthalic acid, perbenzoic acid, can be used, either as acid or in the form of their salts.

When a system comprising a bleach precursor is used, this system comprises a bleaching agent which reacts with a bleach precursor to form a peracid in solution faster than the sodium perborate/TAED system. By faster is meant that the precursor will have a rate of peroxy acid release of at least 2 (two) times, preferably at least 5 (five) times faster than TAED under the same conditions.

Typical examples of such systems are sodium perborate with sodium nonanoyloxy benzene sulphonate or sodium trimethyl hexanoyloxy benzene sulphonate or sodium acetoxy benzene sulphonate or sodium benzoyloxy benzene sulphonate.

The preferred systems of the present invention are sodium perborate with sodium nonanoyloxy benzene sulphonate, diperoxy dodecane dioic acid or monopersulphate.

In general, the amount of the bleaching system in the composition varies from 1–50%, usually from 5–40% by weight. When a bleach precursor is present, the molar ratio of the bleach precursor to the percompound such as sodium perborate varies from 1:1 to 1:35, preferably from 1:2 to 1:20. Mixtures of various bleaching agents and various bleach precursors in accordance with the invention can also be used.

The compositions of the present invention may furthermore contain one or more detergent active materials, such as soaps, anionic, nonionic, cationic and zwitterionic synthetic detergents or mixtures thereof. Usually the amount of detergent active material present in the composition will range from 1–50%, preferably 2–40% and particularly preferably 5–30% by weight. Suitable examples of detergent active materials can be found in Schwartz, Perry and Berch "Surface Active Agents and Detergents", Vol I (1949) and Vol II (1958) and M Schick "Nonionic Surfactants" Vol I (1967).

The compositions may furthermore include the usual detergent ingredients in the usual amounts. They may be unbuilt or built, and may be of the zero-P type (i.e., not containing phosphorus-containing builders). Thus, the compositions may contain from 1–60%, preferably from 5–30% by weight of one or more organic and/or inorganic builders. Typical examples of such builders are the alkali metal ortho-, pyro- and tri-polyphosphates, alkali metal carbonates, either alone or in admixture with calcite, alkali metal citrates, alkali metal nitrilotriacetates, carboxymethyloxy succinates, zeolites, polyacetal carboxylates and so on.

The compositions may furthermore comprise lather boosters, foam depressors, anti-corrosion agents, soil-suspending agents, sequestering agents, anti-soil redeposition agents, perfumes, dyes, stabilizing agents for the enzymes and bleaching agents and so on. They may also comprise enzymes other than lipases, such as proteases, amylases, oxidases and cellulases. In this respect it has been found that, whereas proteases, are often affected by strong bleaches, in the present invention, when used together with the lipases of the present invention, the overall performance of the enzyme system is often not significantly affected.

In general, the compositions may comprise such other enzymes in an amount of 0.01–10% by weight. For proteases, the amount, expressed in proteolytic activity, is usually from 0.1–50 GU/mg based on the final composition.

A GU is a glycine unit, which is the amount of proteolytic enzyme which under standard incubation conditions produces an amount of terminal NH2-groups equivalent to 1 microgram/ml of glycine.

The compositions of the present invention can be formulated in any desired form, such as powders, bars, pastes, liquids, etc.

The invention will further be illustrated by way of Example. The invention described herein extends to modifications and variations as will be apparent to the skilled reader, and combinations and subcombinations of the features mentioned herein.

EXAMPLE 1

The stability of various lipases in the presence of a bleaching system was measured as follows:

To a solution of 4 g/l of a detergent composition* and 0.03 g/l Dequest 2041 in water with a hardness of 30° FH and a temperature of 30° C., an amount of lipase is added to obtain 15–20 lipase units/ ml.
The detergent composition had the following formulation:

The pH is adjusted with NaOH to pH 10.0 at 30%C. At t=0 a bleach system is added:

a) 292 mg/l TAED (65% pure) and 700 mg/l sodium perborate monohydrate or
b) 1880 mg/l DPDA (12% pure) or
c) 822 mg/l SNOBS (80% pure) and 1500 mg/l sodium perborate monohydrate or
d) 506 gm/l MPS (in the form of the commercial product Caroate R) or
e) 475 mg/l P15 (95% pure) and 700 mg/l sodium perborate monohydrate.

This yields 1.5 mmolar peracid in solution for all bleach systems. The lipase stability is measured by determining the residual lipase activity with the pH-stat. method.

| | |
|---|---|
| Dequest 2041 | ethylene diamine tetra (methylene phosphonic-acid) |
| TAED | tetraacetyl ethylene diamine |
| DPDA | diperoxy dodecanedioic acid |
| SNOBS | sodium nonanoyloxy benzene sulphonate |
| MPS | sodium monopersulphate |
| P15 | sodium benzoyloxy benzene sulphonate |

| | % by weight |
|---|---|
| Sodium dodecyl benzene sulphonate | 6.5 |
| C14–C15 primary alcohol, condensed with 11 moles of ethylene oxide | 2.0 |
| Sodium stearate | 1.0 |
| Sodium silicate | 7.0 |
| Sodium carboxymethyl cellulose | 0.5 |
| Na2SO4 | 37.0 |
| Pentasodium triphospate | 15.0 |
| Trisodium orthophosphate | 5.0 |
| Fluorescer | 0.2 |
| Ethylene diamine tetraacetic acid | 0.5 |
| Water | 6.2 |
| Dyes | 0.01 |

The following results were obtained:

| Lipase ex. | Trade-name | No bleach activity[1] | | | TAED/perb. activity[1] | | | SNOBS/perb. activity[1] | | |
|---|---|---|---|---|---|---|---|---|---|---|
| | | 10 min | 30 min | t½ (min) | 10 min | 30 min | t½ (min) | 10 min | 30 min | t½ (min) |
| Humicola lanuginosa | Lipolase | 100 | 99 | >30 | 100 | 85 | >30 | 95 | 83 | >30 |
| Pseudomonas gladioli | — | 97 | 97 | >30 | 97 | 92 | >30 | 90 | 80 | >30 |
| Chromobacter viscosum | Toyo Jozo | 100 | 95 | >30 | 100 | 86 | >30 | 80 | 58 | >30 |
| Pseudomonas fluorescens | Amano P | 100 | 98 | >30 | 92 | 100 | >30 | 85 | 80 | >30 |
| Pseudomonas cepacia | ex NOVO | 93 | 90 | >30 | 98 | 94 | >30 | 89 | 81 | >30 |
| Aspergillus niger | Amano AP 6 | 100 | 90 | >30 | 100 | 64 | 43 | 14 | <5 | 2 |
| Mucor Miehei | SP 225 | 67 | 46 | 28 | 95 | 58 | 35 | 81 | 46 | 28 |

| Lipase ex. | Trade-name | DPDA activity[1] | | | MPS activity[1] | | | P15 activity[1] | | |
|---|---|---|---|---|---|---|---|---|---|---|
| | | 10 min | 30 min | t½ (min) | 10 min | 30 min | t½ (min) | 10 min | 30 min | t½ (min) |
| Humicola lanuginosa | Lipolase | 95 | 70 | >30 | 94 | 72 | >30 | 100 | 96 | >30 |
| Pseudomonas gladioli | — | 100 | 99 | >30 | 89 | 80 | >30 | 92 | 77 | >30 |
| Chromobacter viscosum | Toyo Jozo | 107 | 98 | >30 | 85 | 62 | >30 | 93 | 63 | >30 |
| Pseudomonas fluorescens | Amano P | 109 | 100 | >30 | 89 | 85 | >30 | 102 | 83 | >30 |
| Pseudomonas cepacia | ex NOVO | 100 | 98 | >30 | 97 | 96 | >30 | 95 | 84 | >30 |
| Aspergillus niger | Amano AP | 62 | <5 | 12 | 78 | 40 | 24 | 30 | 9 | 7 |
| Mucor Miehei | SP 225 | 86 | 68 | >30 | 13 | 5 | 4 | 73 | 44 | 26 |

[1] residual lipase activity (% of input)
t½ = half life time

EXAMPLE 2

Example 1 was repeated, but now in the presence of 20 GU (glycine unit)/$_{ml}$ Savinase ®, a proteolytic enzyme ex NOVO.
The following results were obtained:

| Lipase | No bleach activity[1] | | | TAED/perb. activity[1] | | | SNOBS/perb. activity[1] | | |
|---|---|---|---|---|---|---|---|---|---|
| | 10 min | 30 min | t½ (min) | 10 min | 30 min | t½ (min) | 10 min | 30 min | t½ (min) |
| | | | | | | | * | | |
| Lipolase | 100 | 100 | >30 | 100 | 88 | >30 | 95 | 85 | >30 |
| Ps. gladioli | 81 | 56. | 37 | 76 | 51 | 31 | 76 | 55 | 36 |
| Amano P | 51 | 17 | 10 | 56 | 20 | 12 | 40 | 16 | 6 |
| Ps. cepacia | 65 | 35 | 18 | 72 | 38 | 19 | 65 | 34 | 19 |
| Toyo Jozo | 79 | 48 | 30 | 71 | 38 | 18 | 72 | 47 | 28 |
| Amano AP6 | 96 | 83 | >30 | 82 | 38 | 25 | <5 | <5 | 3 |
| Esterase MM | 64 | 21 | 13 | 38 | 15 | 8 | 43 | 12 | 8 |

| Lipase | DPDA activity[1] | | | MPS activity[1] | | | P15 activity[1] | | |
|---|---|---|---|---|---|---|---|---|---|
| | 10 min | 30 min | t½ (min) | 10 min | 30 min | t½ (min) | 10 min | 30 min | t½ (min) |
| | ** | | | *** | | | **** | | |
| Lipolase | 96 | 90 | >30 | 94 | 72 | >30 | 100 | 96 | >30 |
| Ps. gladioli | 90 | 70 | >60 | 63 | 47 | 20 | 81 | 42 | 26 |
| Amano P | 60 | 24 | 12 | 43 | 27 | 8 | 55 | 15 | 11 |
| Ps. cepacia | 59 | 42 | 18 | 54 | 32 | 12 | 65 | 28 | 17 |
| Toyo Jozo | 82 | 52 | 33 | 38 | 22 | 8 | 74 | 29 | 17 |
| Amano AP6 | 61 | 15 | 12 | 91 | 79 | >30 | 55 | 24 | 11 |
| Esterase MM | 68 | 25 | 16 | 10 | <5 | 5 | 74 | 25 | 17 |

*in an experiment with Kazusase, a proteolytic enzyme ex Showa Denko, the following results were obtained: 95% 84% > 30.
**with Alcalase instead of Savinase, the results were as follows: 97% 93% > 30.
***with Alcalase instead of Savinase, the results were as follows: 90% 76% > 30.
****with Kazusase instead of Savinase, the results were as follows: 99% 89% > 30.
[1] residual lipase activity (% of input)
t½ = half life time

We claim:

1. A detergent composition comprising from 1-50% by weight of one or more detergent-active materials, from 0-60% by weight of a builder, from 1-50% by weight of a bleaching agent and lipolytic enzyme in an amount of 0.005-100 lipolytic units per milligram of the composition, characterised in that the bleaching agent is based on an inorganic or organic peracid or salt thereof which is stronger than peracetic acid or comprises a bleaching agent and a bleach precursor which yields, on perhydrolysis, a peracid faster than the system comprising sodium perborate+tetraacetyl ethylene diamine, and the lipolytic enzyme is a lipase produced by cloning by rDNA technique the gene encoding the lipase produced by *Humicola lanuginosa* (syn. *Thermomyces lanuginosus*) and expressing the gene in *Aspergillus oryzae* as host.

2. A composition according to claim 1, characterised in that the bleaching agent is an alkali metal persulphate.

3. A composition according to claim 1 characterised in that the bleaching agent is selected from the group consisting of diperoxy dodecanedioic acid, diperoxy tetradecanedioic acid, diperoxyhexadecane dioic acid, mono- and diperazelaic acid, mono- and diperbrassylic acid, monoperoxy phthalic acid, perbenzoic acid, and their salts.

4. A composition according to claim 1, characterized in that the bleaching agent comprises a bleaching agent and a bleach precursor which forms a peracid in solution at least two times faster than tetraacetyl ethylene diamine under the same conditions.

5. A composition according to claim 4, characterised in that the bleaching agent comprises sodium perborate and a bleach precursor selected from the group consisting of sodium nonanoyloxy benzene sulphonate, sodium trimethyl hexanoyloxy benzene sulphonate, sodium acetoxy benzene sulphonate and sodium benzoyloxy benzene sulphonate.

6. A composition according to claim 1, characterized in that it further contains a proteolytic enzyme in an amount of 0.1-50 GU/mg of the composition.

* * * * *